United States Patent [19]

Merianos et al.

[11] Patent Number: 5,188,818

[45] Date of Patent: Feb. 23, 1993

[54] TOOTHPASTE COMPOSITION CONTAINING STRONTIUM SALT OF MALEIC ANHYDRIDE-METHYL VINYL ETHER COPOLYMER

[75] Inventors: John J. Merianos, Middletown; Paul Garelick, South Plainfield; Herbert A. Lieberman, Livingston, all of N.J.

[73] Assignee: ISP Investments Inc., Wilmington, Del.

[21] Appl. No.: 859,786

[22] Filed: Mar. 30, 1992

[51] Int. Cl.$^5$ .............................................. A61K 7/16
[52] U.S. Cl. .................................................... 424/49
[58] Field of Search ..................................... 424/49-58

[56] References Cited

U.S. PATENT DOCUMENTS

| | | | |
|---|---|---|---|
| 4,758,630 | 7/1988 | Shah et al. | 525/207 |
| 4,965,067 | 10/1990 | Wietfeldt | 424/52 |
| 4,992,258 | 2/1991 | Mason | 424/49 |
| 5,073,604 | 12/1991 | Holeva et al. | 525/327.8 |

FOREIGN PATENT DOCUMENTS 265916  5/1988  European Pat. Off. .

*Primary Examiner*—Shep K. Rose
*Attorney, Agent, or Firm*—Walter Katz; Marilyn J. Maue; Joshua J. Ward

[57] ABSTRACT

A toothpaste composition is provided which includes the strontium salt of maleic anhydride-methyl vinyl ether copolymer. This ingredient is capable of desensitizing the nerve endings of a tooth in saliva or water because of an extension of the contact time of the strontium on the tooth surface.

4 Claims, No Drawings

TOOTHPASTE COMPOSITION CONTAINING STRONTIUM SALT OF MALEIC ANHYDRIDE-METHYL VINYL ETHER COPOLYMER

BACKGROUND OF THE INVENTION

1. Field of the Invention

This invention relates to toothpaste compositions, and, more particularly, to a toothpaste dentifrice with strontium capable of desensitizing the nerve endings of a tooth in saliva or water because of an extension of the contact time of the strontium ions on the tooth surface.

2. Description of the Prior Art

Rosenthal, in U.S. Pat. No. 3,122,483, issued Feb. 25, 1964, described a water-containing toothpaste for tee treatment of hyper-sensitive dentin characterized by including therein water-soluble strontium compounds that release strontium ions from solution. The strontium compounds disclosed were the strontium chloride, acetate, bromise, lactate, iodide, nitrate and salicylate.

However, this and other patents, publications and commercial products for treating hyper-sensitive dentin have inherent disadvantages: (1) the strontium compound may not provide an adequate concentration of strontium ions in aqueous solution, i.e. the strontium compound may not be very soluble in water; (2) even if present in water, the strontium ions may not adhere particularly well to the tooth surface where it can perform its desensitizing action; (3) accordingly, the contact time of strontium on the tooth may be quite short, and thereby its effectiveness diminished; (4) the strontium ions are susceptible to being precipitated out of solution by the presence of other components in the composition; and (5) inorganic strontium compounds do not provide a film on the tooth surface.

Accordingly, the object of the present invention is to provide an improved toothpaste composition which overcomes the deficiencies of the prior art and commercial products for treating pain caused by sensitive teeth.

SUMMARY OF THE INVENTION

What is provided herein is a toothpaste composition for desensitizing the nerve endings of a tooth in saliva or water because of an extension of the contact time of the strontium on the tooth surface. This action is due to two properties that characterize the strontium salt, namely good water solubility and secondly being capable of forming an adherent film on the surface of the tooth. These properties of the strontium salt enhance its desensitizing activity as compared to inorganic strontium compounds alone or in combination with less water soluble polymers.

In the preferred form of the invention, the toothpaste composition contains about 1-20%, most preferably, about 5-10%, by weight of the composition, of the strontium salt of the maleic anhydride-methyl vinyl copolymer known commercially as Gantrez ® (International Specialty Products).

DETAILED DESCRIPTION OF THE INVENTION

The active ingredient in the toothpaste composition of the invention is the strontium salt of the copolymer of maleic anhydride and methyl vinyl ether. This polymer salt is synthesized by neutralizing the copolymer itself with a suitable strontium compound, such as strontium hydroxide, in aqueous solution, and recovering the desired strontium salt by evaporation of the solution.

This strontium salt has the following combination of advantageous properties:

(1) water soluble;
(2) adheres to plaque;
(3) forms a film on teeth;
(4) performs its desensitizing action on teeth for an extended time period;
(5) not susceptible to precipitation from solution; and
(6) capable of being formulated into either regular or clear toothpaste compositions.

Typical toothpaste formulations according to the invention are the following:

| No. | Phase | Regular Toothpaste Ingredient | % by wt. |
|---|---|---|---|
| 1 | A | Glycerin 96% | 10.00 |
| 2 | A | CMC-9M31XF | .85 |
| 3 | B | Sorbitol 70% | 12.00 |
| 4 | B | Deionized water | 24.48 |
| 5 | B | Tetrasodium pyrophosphate, anhyd. | .25 |
| 6 | B | Sodium saccharin | .20 |
| 7 | B | Sodium Benzoate | .50 |
| 8 | B | Strontium Salt of Gantrez ® | 7.5 |
| 9 | C | Sodium hydroxide (50%) | .05 |
| 10 | D | Dicalcium phosphate, dihydrate | 41.7 |
| 11 | E | Flavor | 1.00 |
| 12 | F | Sodium lauryl sulfate | 1.20 |
|   |   | Total | 100.00 | pH: 7.21
Viscosity: 136 M CPS

Manufacturing Procedure: Add glycerin to vacuum mixer. Slowly sprinkle in CMC with rapid agitation. In a separate vessel dissolve ingredients of Phase B in Phase B water. Add to batch. Add Phase C. Cover and mix under 27-29 inches of vacuum for 5-10 minutes. Add Phase D. Mix under vacuum for 30 minutes. Add E and F mix under vacuum for 5 minutes.

| No. | Phase | Clear Toothpaste Ingredient | % by wt. |
|---|---|---|---|
| 1 | A | Glycerin 96% | 14.00 |
| 2 | A | CMC-9M31XF | .30 |
| 3 | B | Sorbitol 70% | 41.56 |
| 4 | C | Sodium saccharin | .20 |
| 5 | C | Sodium Benzoate | .08 |
| 6 | C | Strontium Salt of Gantrez ® | 7.5 |
| 7 | C | Deionized water | 5.00 |
| 8 | D | Polyethylene glycol-32 | 5.00 |
| 9 | E | Abrasive silica | 7.00 |
| 10 | E | Thickening silica | 7.50 |
| 11 | F | Glycerin 96% | 5.50 |
| 12 | F | Sodium lauryl sulfate | 1.25 |
| 13 | F | Polysorbate-20 | 2.00 |
| 14 | F | FD&C blue #1 (1% aqueous) | .05 |
| 15 | F | FD&C yellow #5 (1% aqueous) | .10 |
| 16 | F | Flavor | .70 |
| 17 | F | Alcohol SD38B | 2.00 |
|   |   | Total | 100.00 |

Manufacturing Procedure: Add glycerin to vacuum mixer. Slowly sprinkle in CMC with rapid agitation. In a separate vessel dissolve ingredients of Phase B in Phase B water. Add to batch. Add Phase C. Cover and mix under 27-29 inches of vacuum for 5-10 minutes. Add Phase D. Mix under vacuum for 30 minutes. Add E and F mix under vacuum for 5 minutes.

While the invention has been described with particular reference to certain embodiments thereof, it will be understood that changes and modifications may be made which are within the skill of the art. Accordingly, it is intended to be bound only by the following claims, in which:

What is claimed is:

1. A toothpaste composition containing about 1-20% by weight of the strontium salt of the copolymer of maleic anhydride and methyl vinyl ether.

2. A toothpaste composition according to claim 1 wherein said amount is about 5-10%.

3. A toothpaste composition according to claim 1 wherein said amount is about 7.5%.

4. A toothpaste composition according to claim 1 which contains water.

* * * * *